United States Patent
Zeng

[11] Patent Number: 6,120,351
[45] Date of Patent: Sep. 19, 2000

[54] AUTOMATIC MACHINABILITY MEASURING AND MACHINING METHODS AND APPARATUS THEREFOR

[75] Inventor: Jiyue Zeng, Bellevue, Wash.

[73] Assignee: Ingersoll-Rand Company, Woodcliff Lake, N.J.

[21] Appl. No.: 09/144,034

[22] Filed: Aug. 31, 1998

[51] Int. Cl.[7] .................................................. B24C 3/22
[52] U.S. Cl. ................................ 451/28; 451/40; 451/2; 451/78
[58] Field of Search .............................. 451/2, 3, 40, 75, 451/78, 80, 99, 102

[56] References Cited

U.S. PATENT DOCUMENTS

| | | | |
|---|---|---|---|
| 3,516,204 | 6/1970 | Kulischenko | 451/2 |
| 3,769,753 | 11/1973 | Fleischer | 51/11 |
| 3,994,079 | 11/1976 | Lamb | 451/40 |
| 4,380,138 | 4/1983 | Hofer | 451/40 |
| 4,412,402 | 11/1983 | Gallant | 451/40 |
| 4,753,051 | 6/1988 | Tano et al. | 451/3 |
| 4,941,955 | 7/1990 | Schuster | 204/129.5 |
| 4,966,059 | 10/1990 | Landeck | 83/53 |
| 5,166,885 | 11/1992 | Thompson | 451/2 X |
| 5,207,533 | 5/1993 | Federspiel et al. | 405/156 |
| 5,222,332 | 6/1993 | Mains, Jr. | 451/40 X |
| 5,341,608 | 8/1994 | Mains, Jr. | 51/320 |
| 5,401,204 | 3/1995 | Shank | 451/40 |
| 5,501,104 | 3/1996 | Ikeda et al. | 73/629 |
| 5,700,181 | 12/1997 | Hashish et al. | 451/40 |

FOREIGN PATENT DOCUMENTS

| | | | |
|---|---|---|---|
| 361004670 | 1/1986 | Japan | 451/40 |

OTHER PUBLICATIONS

Zeng, et al., "Quantitative Evaluation of Machinability in Abrasive Waterjet Machining," Precision Machining: Technology and Machine Development and Improvement; PED–vol. 58; pp. 169–179 (1992).

Jiyue Zeng and Jose P. Munoz, "Intelligent Automation of AWJ Cutting for Efficient Production," Proceedings of the 12th International Symposium on Jet Cutting Tech., pp. 401–408 BHRA, Rouen, France (1994).

Smartline™ Expert System Software for Fluid Jet Cutting; Ingersoll–Rand® Brochure, 2 pages (1996).

J. Zeng, J. Munoz, and Ihab Kain, "Milling Ceramics with Abrasive Waterjets—An Experimental Investigation," Proceedings of the Ninth American Waterjet Conference: Waterjet Technology Ass'n., Dearborn, MI, pp. 93–108. (Aug. 23–26, 1997).

Zeng, J. and Kim, T., "The Machinability of Porous Material by a High Pressure Abrasive Waterjet," Proceedings of the Winter Annual Meeting of ASME, San Francisco, U.S.A., pp. 37–42 (1989).

(List continued on next page.)

*Primary Examiner*—David A. Scherbel
*Assistant Examiner*—Anthony Ojini
*Attorney, Agent, or Firm*—Leon Nigohosian, Jr.

[57] ABSTRACT

A method for measuring the machinability of a material which includes piercing a hole through a material to be tested while simultaneously measuring a pierce time duration, T, of the piercing step, and calculating a machinability number from the pierce time duration. Also provided are methods for determining the machining speed of a material and for machining a material which calculate a machining speed for a material based upon the machinability number of the material. The methods used to measure the machinability number and calculate a machining speed for a particular material can include any combination of machining operations, including but not limited to AWJ cutting processes. Also provided is an apparatus which detects the time duration a piercing force takes to create a pierce-through condition through a material. The apparatus includes any of a pressure sensor, an acoustic sensor, an optical sensor, a load cell, a mechanical switch, and combinations thereof to measure the pierce-time duration.

27 Claims, 5 Drawing Sheets

OTHER PUBLICATIONS

Ohlsson, et al., "Optimisation of the Piercing or Drilling Mechanism of Abrasive Water Jets," Proceedings of the 11th Int'l Conference on Jet Cutting Technology, Scotland, pp. 359–370 (Sep. 1992).

O'Keefe Controls Co. "Air Proximity Sensor" Brochure, Form OK–098 4 pages (1993).

O'Keefe Controls Co. "Products Manufactured" Brochure, Form OK–096 R1, 2 pages (1994).

O'Keefe Controls Co. "Accessories for Pneumatic Controls", Brochure, Form OK–063R3, 2 pages (1996).

O'Keefe Controls Co. Air Proximity Sensor System Electric Output Brochure, Form OK–164, 2 pages (not dated).

O'Keefe Controls Co. "Air Proximity Sensor System Pneumatic Output" Brochure, Form OK–165, 2 pages (not dated).

Quest 2800 Impulse Integrating Sound Level Meter, Quest Technologies Brochure, p. 35 (not dated).

Motion Control Systems, Inc. Acroloop ACR2000 (1–4 Axes Controller), Newsletter, 6 pgs. (Jun. 1997).

"Load Cells" Sens–All, Inc. Advertisement, 1 pg (not dated).

"Abrasive Water Jets for Demilitarization of Explosive Materials" D. Miller, 8th American Water Jet Conference, p. 457 (not dated).

"Selecting and Justifying a Laser Cutting System: Examining the Benefits of Lasers", Sheet Metal Cutting, pp. 20–23 (not dated).

"New Developments in Laser Fusion Cutting," Sheet Metal Cutting, pp. 68–69 (not dated).

"Cutting with Precision Plasma Technology: Stabilized Jet Helps Improve Cut Quality", Sheet Metal Cutting, pp. 72,73 (not dated).

AUTOMATIC MACHINABILITY MEASURING AND MACHINING METHODS AND APPARATUS THEREFOR

BACKGROUND OF THE INVENTION

This invention relates generally to machining methods and apparatus and more particularly to methods and apparatus for abrasive waterjet machining of engineering materials.

The machinability number is a property of a specific material which varies depending on the type of machining operation, such as cutting, to be performed and is related to a number of materials properties. For abrasive waterjet machining of ductile materials, the machinability number is related primarily to flow stress of the material. For abrasive waterjet machining of brittle materials, the machinability is related to the fracture energy, grain size (or flow distribution for materials such as glass), modulus of elasticity and Poisson's ratio.

In a jobshop environment in which a variety of workpiece materials are cut using an abrasive waterjet machining process, if a new type of material is to be cut for the first time, a number of empirical cutting tests and calculations must typically be performed to determine the machinability number of the material prior to performing the cutting operation.

J. Zeng et al. in the paper titled "The Machinability of Porous Materials by a High Pressure Abrasive Waterjet," Proceedings of the Winter Annual Meeting of ASME, 1989, pp. 37–42, which paper is incorporated herein by reference, first introduced and incorporated the concept of a "Machinability Number" into parameter prediction methods for determining optimum Abrasive Waterjet (AWJ) machining criteria (e.g., abrasive particle flow rate and cutting speed) to be used in order to achieve a desired surface quality for different materials to be machined.

Some AWJ systems manufacturers and their customers have attempted addressing the problem of determining the machinability numbers of materials by providing databases of machinability number data from trial-and-error, empirical tests a performed by experienced AWJ operators on specific customer materials. This, however, involves considerable effort which is both costly and time-consuming. Such databases are also cumbersome and tedious to use.

The development of computer software has facilitated the use of databases of empirically obtained machinability number data to calculate the optimum operating criteria for materials for which the machinability number has been previously obtained.

In the case a new material for which the machinability number is unknown is to be cut or otherwise machined, the computer software may also be used to guide and assist an operator in conducting the empirical tests required to determine the machinability number from test pieces of the material.

The trial-and-error testing required to obtain machinability number data is wasteful, however, because it requires the use of numerous test pieces of material. Moreover, the testing is costly and time-consuming because it requires an AWJ machine operator to manually perform and evaluate the results of the testing, input the resultant empirical results, and program the machining parameters required for a subsequent machining operation to be performed.

The foregoing illustrates limitations known to exist in present machining methods and apparatus. Thus, it is apparent that it would be advantageous to provide an alternative directed to overcoming one or more of the limitations set forth above. Accordingly a suitable alternative is provided including features more fully disclosed herein.

SUMMARY OF THE INVENTION

The present invention provides a method for measuring the machinability of a material which includes piercing a hole through a material to be tested while simultaneously measuring a pierce time duration, T, of the piercing step, and calculating a machinability number from the pierce time duration. Also provided are methods for determining the machining speed of a material and for machining a material which calculate a machining speed for a material based upon the machinability number of the material. The methods used to determine the machinability number and calculate a machining speed for a particular material can include a variety of machining operations including, but not limited to, AWJ cutting processes.

Also provided is an apparatus which detects a pierce-through condition through a material made by a piercing force and the time duration the piercing force takes to create the pierce-through condition. The apparatus includes any of a pressure sensor, an acoustic sensor, an optical sensor, a load cell, a mechanical switch, and combinations thereof to measure the existence of a pierce-through condition. Apparatus including a controlling unit are also provided for detecting and maintaining the gap distance between a nozzle assembly for a machining process and a workpiece to be machined which, respectively, obtains and maintains a predetermined stand-off distance between a nozzle of the nozzle assembly and a workpiece for a machining process. The controlling unit can further determine the thickness of a workpiece to be machined based upon the position of the nozzle assembly upon establishing the predetermined gap distance with the workpiece.

It is to be understood that both the foregoing general description and the following detailed description are exemplary, but are not restrictive, of the invention. The foregoing and other aspects will become apparent from the following detailed description when read in conjunction with the accompanying drawing figures.

DETAILED DESCRIPTION OF THE INVENTION

The apparatus and method of the present invention are best understood from the following detailed description when read in connection with the drawing figures in which like reference numerals refer to like elements throughout. It is emphasized that according to common practice, the various dimensions of the apparatus shown in the drawings are not to scale.

Figure 1:
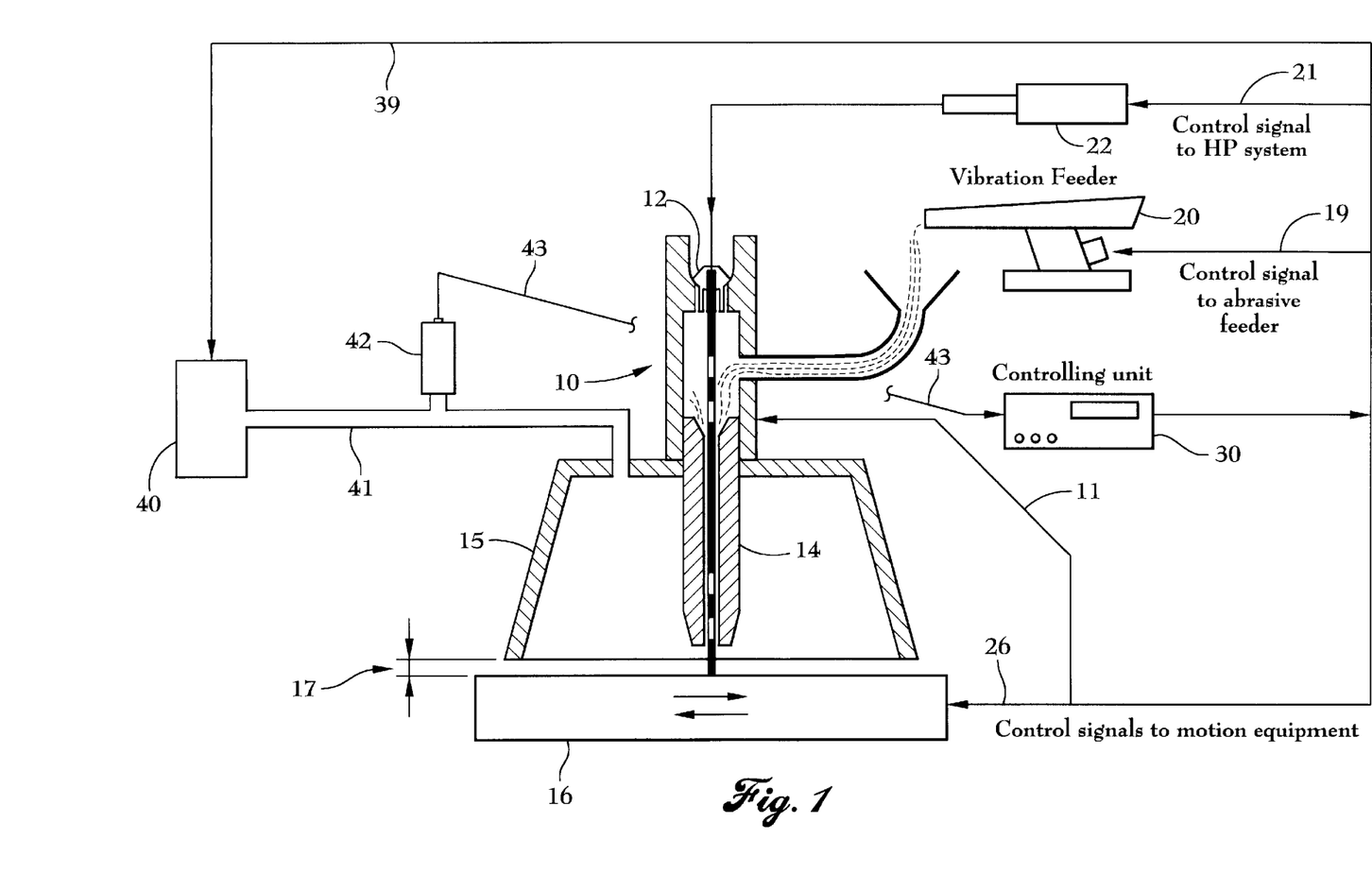
FIG. 1 is a general symbolic diagram of the components of an abrasive waterjet system according to the present invention.

Referring now to the drawing, FIG. 1 shows a broad system diagram of an embodiment of the invention as applied to an abrasive waterjet (AWJ) system. Abrasive water jet (AWJ) processes employ abrasive materials entrained into a high-pressure waterjet to perform a variety of cutting and other machining operations on a variety of materials. The high-energy waterjet beam utilized combines a rapid erosion of a workpiece material by high speed solid particle impacts with rapid cooling provided by a waterjet. In AWJ cutting operations an abrasive waterjet pierces through the thickness of and is then moved along a material to be cut.

Briefly, shown in FIG. 1 is a nozzle assembly 10 comprised of an orifice 12 and a focusing tube 14 which applies a mixture of high pressure water and abrasive to a moving workpiece 16. Nozzle assembly 10 is preferably supplied abrasive from an optional vibration feeder 20 and high pressure water from a water source 22. Although shown using a vibration feeder, it is understood that other types of feeding devices, which are known and will be readily recognized by those having ordinary skill in the art, may be used for this purpose.

In performing AWJ processes, a number of parameters such as water pressure, abrasive particle size, abrasive flow rate, and the dimensions of the waterjet nozzle orifice are varied depending on the type of material to be cut. A controlling unit 30 is provided which controls the feed from vibration feeder 20 and the feed supply of high pressure water from water source 22. Prior to performing an AWJ cutting operation, controlling unit 30 is typically preset by a user with the AWJ system operating parameters including "$d_o$", "$d_f$", "P", "A", and "q". The selection of these operating parameters for performing cutting operations using an AWJ apparatus are described in detail below.

In operation, as high pressure water and abrasives are supplied to the nozzle, the workpiece 16 is moved back and forth by positioning equipment (not shown), as is known in the art, which maneuvers the workpiece for the desired cutting operation responsive to a control signal provided by controlling unit 30. As described in detail below, controlling unit 30 receives input on the operating conditions of the AWJ system and calculates optimum cutting speeds "$u_c$" for the material of workpiece 16 and accordingly controls the motion of workpiece 16 to provide the desired speed. Controlling unit 30 is preferably a Computerized Numerical Controller (CNC) which is available and known to those in the art and may include, e.g., the Model ACR 2000 motion controller which is available from Acroloop Motion Control Systems, Inc., Chanhassen, Minn.

AWJ CUTTING EQUATIONS AND OPERATING PARAMETERS

As reported by J. Zeng and J. P. Munoz in the article titled "Intelligent Automation of AWJ Cutting for Efficient Production," Proceedings of the 12th International Symposium on Jet Cutting Technology, BHRA, Rouen, France, 1994, pp. 401–408 which is incorporated herein by reference, the traverse cutting speed "$u_c$" at which a waterjet cuts through a particular material during an abrasive waterjet cutting operation may be estimated according to the following equation:

$$u_c = \left( \frac{N_{mc} \cdot P^{1.593} \cdot d_O^{1.374} \cdot A^{0.343}}{C \cdot q \cdot h \cdot d_f^{0.618}} \right)^{1.15} \quad \text{[Eqn. 1]}$$

where "$d_o$" is the bore diameter (inches) of orifice 12; "$d_f$" is the bore diameter (inches) of focusing tube 14; "P" is the water pressure (ksi) to be provided by high-pressure water source 22; and "A" is the abrasive flow rate (lbs/min) to be provided to nozzle assembly 10 by vibration feeder 20. "C" is a constant (which is 180.33 when calculating cutting speed using dimensions for an inch-unit system) and "q" is the quality index which is a measure of the desired surface condition of the resultant cut surfaces, "h" is the workpiece thickness, and "$N_{mc}$" is the machinability number for cutting the workpiece material.

Typical operating parameters for performing an AWJ cutting process using the apparatus described above are as follows:

Waterjet pressure (P): default set to 50 ksi, but varies depending on water pump capacity Orifice Bore Diameter ($d_o$): default set to 0.014 in, but varies depending on water pump capacity Focusing Tube Bore Diameter ($d_f$): use tube having inner bore diameter approximately equal to 3. $d_o$ (i.e., 0.042 inches)

Abrasive Flow Rate (A): set to 1 lb/min (using Barton garnet #80)

For a cutting operation, the value of "q" in Eqn. 1 above can be chosen between 1 and 5 depending on the desired quality level. As described by J. Zeng et al. at pp. 174–175 of the article titled "Quantitative Evaluation of Machinability in Abrasive Waterjet Machining," PED-Vol. 58, Precision Machining: Technology and Machine Development and Improvement, ASME 1992, pp. 169–179, which article is incorporated herein by reference, the various quality levels are generally defined for engineering materials as follows:

| Quality Level | Description |
| --- | --- |
| q = 1 | Criteria for Separation cuts- preferably q > 1.2 should be used |
| q = 2 | Rough surface finish with striation marks at lower half surface |
| q = 3 | Smooth/Rough transition criteria- Slight striation marks may appear |
| q = 4 | Striation-free for most engineering materials |
| q = 5 | Very smooth surface finish |

The thickness "h" is dictated by the size of the workpiece to be cut and is measured and inputted into controlling unit 30 either manually by a user or automatically using a thickness sensor according to the present invention as described in detail below.

The machinability number "$N_{mc}$" depends upon the type of the material upon which a cutting operation is to be performed. Because the machinability number is a property of a specific material, it must be determined prior to performing a cutting operation on a workpiece made of a type of material which has not been cut before. According to the present invention, the need for predetermining a machinability number for a material by multiple trial-and-error tests prior to performing a machining operation may be eliminated by the automatic machinability measuring and machining methods and the apparatus therefor provided herein.

The present inventor has discovered that the machinability number "$N_{mc}$" for a cutting operation on a material is inversely related to the time "T" required by an AWJ waterjet to pierce through a material using a circular piercing motion having a thickness "h" according to the following empirical equation:

$$N_{mc} = \left( \frac{C_{tc} \cdot h^{1.786}}{T \cdot P^{1.757} \cdot d_O^{2.072}} \right) \quad [\text{Eqn. 2}]$$

where "$C_{tc}$" is a constant (which is 54.7 when calculating cutting speed using dimensions for an inch-unit system) and "P" is the waterjet pressure (ksi) and "$d_o$" the orifice diameter (inches) of the water jet nozzle. Thus, by making an initial test hole through an unknown material and incorporating a means for detecting the moment the waterjet pierces through the material, the machinability number for cutting can be automatically calculated for a workpiece based upon the piercing time. Moreover, if the piercing operation is performed on the actual workpiece to be cut the test hole may be used as a starting hole for the cutting operation. In this manner, the need for any preliminary testing on scrap material may be eliminated by a "drop-and-cut" operation in which a workpiece of unknown material is simply placed on the AWJ apparatus and cut by an automated process.

APPARATUS FOR DETECTING PIERCE-THROUGH OF A WORKPIECE

In order to detect the moment a waterjet pierces a workpiece, a number of means may be incorporated. According to one embodiment of the present invention, as shown in FIG. 1 nozzle assembly 10 includes a nozzle shield 15 surrounding the focusing tube 14. Nozzle shield 15 is connected to and in fluid communication with an air or other gas supply 40 via a conduit 41. A pressure sensor 42 is connected to conduit 41 and located between nozzle shield 15 and air supply 40 for sensing the pressure conditions inside nozzle shield 15 and providing a pressure sensor signal 43 to controlling unit 30.

OPERATION FOR PERFORMING AUTOMATED AWJ CUTTING

Figure 4:
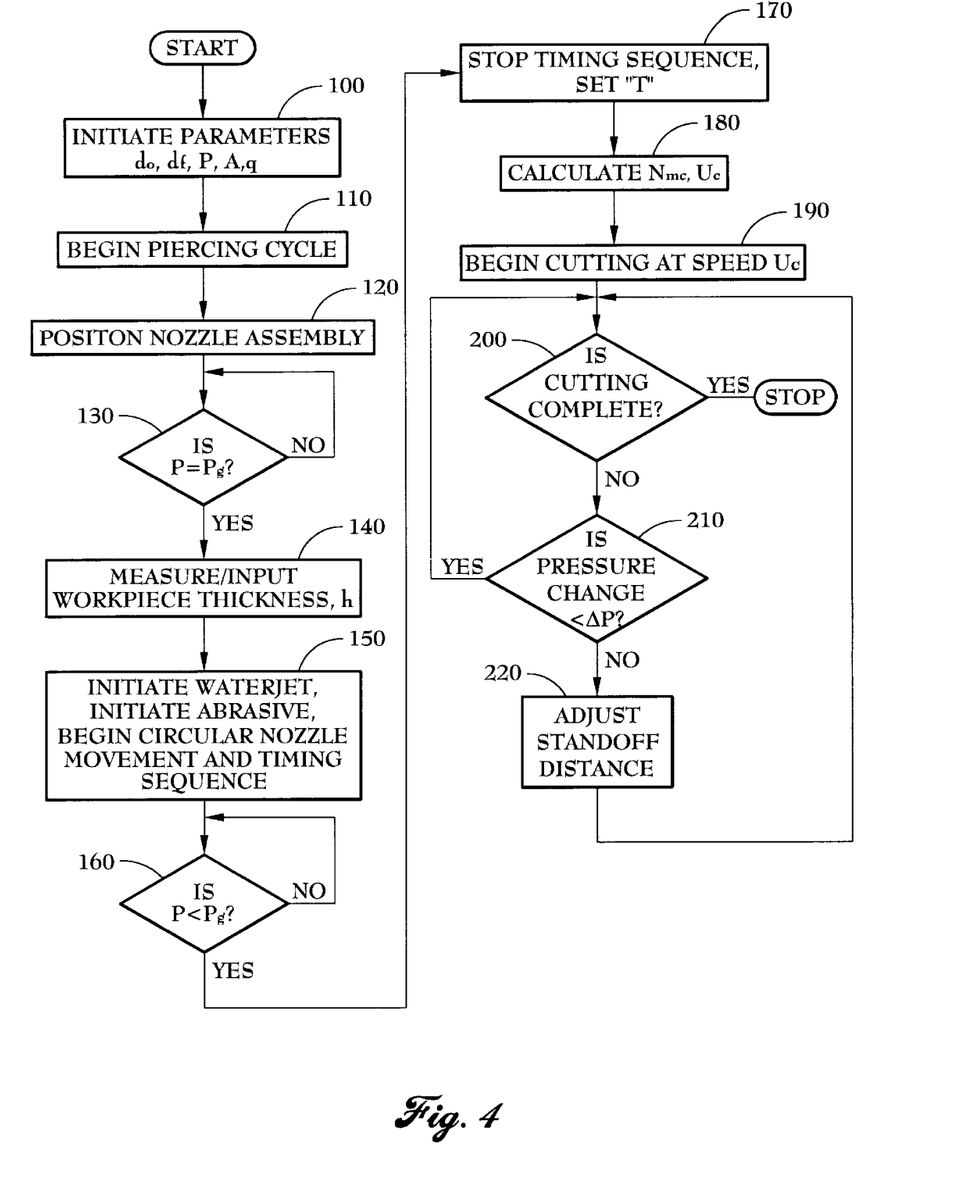
FIG. 4 is a program flow chart for a software program resident in the programmable controlling unit of FIG. 1 for performing a cutting method according to an embodiment of the present invention.

Operation of the AWJ apparatus shown in FIG. 1 will be described with respect to performing an AWJ cutting operation according to the automated method of the present invention. Turning to the flow diagram in FIG. 4, controlling unit 30 is initialized in Step 100 by inputting the specific AWJ system operating parameters including "$d_o$", "$d_f$", "P", "A", and "q" prior to beginning an AWJ cutting cycle.

A. Positioning Nozzle Assembly at a Predetermined Stand-Off Distance

Controlling unit 30, upon receiving a user instruction to begin a cutting sequence, begins a piercing cycle in Step 110 by generating a control signal 39 in Step 110 to air supply 40 thereby initiating airflow into nozzle shield 15 via conduit 41. Pressure sensor 42 generates and provides to controlling unit 30 a signal similar to that shown in FIG. 2 indicating the pressure condition inside nozzle shield 15 as a function of time. Controlling unit 30 generates a control signal 11 instructing motion equipment (not shown) to lower nozzle assembly in Step 120 to a form an air gap 17 having a predetermined height.

Figure 2:
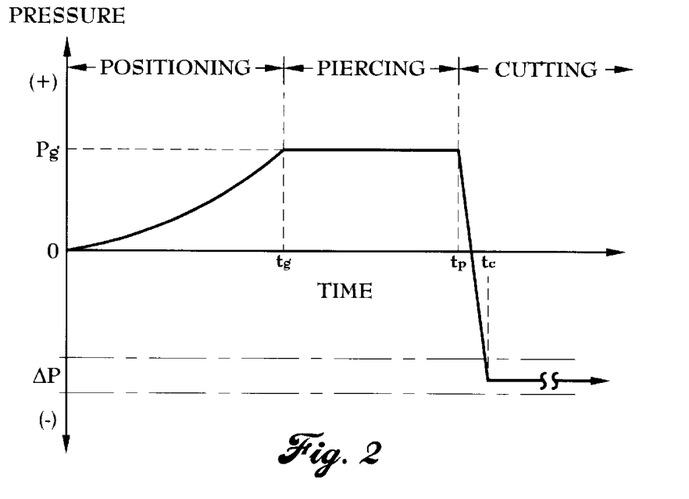
FIG. 2 is a representation of the pressure signal read by a pressure sensor during a cutting method performed according to one embodiment of the present invention.

For a cutting operation, the nozzle shield 15 is set to establish a stand-off distance (i.e., the distance between the focusing tube 14 and workpiece 16) which is about equal to air gap 17, once air gap 17 is established. This is accomplished by using pressure sensor 42 as a proximity switch which monitors in Step 130 the pressure increase caused by the restriction created between workpiece 16 and nozzle shield 15 as it moves toward the target surface. As shown in FIG. 2, the pressure inside nozzle shield 15 increases to a predetermined pressure $P_g$ which is programmed into controlling unit 30 and corresponds to the pressure at which the desired air gap 17 is formed. At this point, when Step 130 detects that nozzle assembly 10 is in position, the controlling unit 30 generates a control signal to stop the motion of the nozzle assembly 10 thereby setting the cutting position (i.e., stand-off distance) and controlling unit 30 also records this position.

B. Determining Workpiece Thickness

As discussed above, the thickness "h" of workpiece 16 may be automatically measured and inputted into controlling unit 30. This is accomplished in Step 140 by comparing the height of nozzle assembly in the cutting position with a known reference position and calculating the thickness of the workpiece. Alternatively, the thickness "h" may be measured manually by the operator and inputted into controlling unit 30 in Step 140.

C. Piercing the Workpiece and Calculating Machinability Number

In Step 150, controlling unit 30 simultaneously generates control signals 21 and 19 to, respectively, initiate the supply of high pressure water from water source 22 and abrasive from vibration feeder 20 to establish an abrasive water jet in water nozzle assembly 10. Controlling unit 30 also begins a timing sequence and sends a control signal 11 to move nozzle assembly 10 at a constant rate (e.g., 50 inches per minute (ipm)) along a circle which, preferably, has a radius equal to the focusing tube diameter, "$d_f$", until workpiece 16 is pierced. During the time the piercing operation is being performed, air supply 40 continues to provide a steady flow of air to nozzle shield 15 while pressure sensor 42 monitors and provides a steady output signal 43 to controlling unit 30 as represented by the horizontal signal between "$t_g$" and "$t_p$" shown in FIG. 2. Upon penetration (i.e., "pierce-through") of the waterjet through workpiece 16, a vacuum is created within nozzle shield 15 which, as shown in FIG. 2, causes a virtually instantaneous drop in the pressure detected by pressure sensor 42 at "$t_p$", which is the moment pierce-through occurs.

Upon detecting the decrease in pressure in Step 160 caused upon pierce-through, controlling unit 30 stops the timing sequence in Step 170 and obtains and records the pierce-through time "T". In Step 180, controlling unit 30 calculates the machinability number "$N_{mc}$" and in turn the cutting speed "$u_c$" according to Eqns. 2 and 1 set forth, respectively, above.

D. Cutting of the Workpiece and Stand-Off Distance Monitoring

The desired cutting operation is then initiated in Step 190 by controlling unit 30 which either sends a control signal 11 to begin horizontal movement of nozzle assembly 10, sends a control signal 26 to begin horizontal movement of workpiece 16, or both, to laterally move nozzle assembly 10 at the calculated cutting speed "$u_c$" relative to workpiece 16. The cutting operation is monitored in Step 200 either visually or automatically (e.g., by a mechanical sensor switch as is known in the art) to detect when the cutting operation is complete. During the cutting operation, air gap 17 between the nozzle assembly 10 and workpiece 16 is preferably monitored in Step 210 for any changes by monitoring the signal provided by pressure sensor 42 for any variation in the signal after time "$t_c$" which represents the time at which pierce-through is completed and cutting begins as shown in FIG. 2. Should any variation above or below a predetermined pressure range (represented as "$\Delta P$" in FIG. 2), which range corresponds to an acceptable stand-off distance tolerance, an error signal is sent by the controlling unit 30 via connection 11 to implement compensation in Step 220 by the motion equipment to adjust the stand-off distance. Alternatively, controlling unit 30 may be programmed to send an error signal via connections 19 and 21 to respectively stop the flow of abrasive and water to interrupt the AWJ operation being performed.

PRESSURE SENSORS AND ALTERNATIVE PIERCE-THROUGH DETECTION DEVICES

With respect to devices which may be incorporated as pressure sensor 42, any sensor which can detect the decrease of pressure which occurs within nozzle shield 15 upon pierce through may be incorporated. An exemplary device includes, but is not limited to, a Model OKC-424 Air Proximity Sensor, available form O'Keefe Controls Co., Monroe, Conn.

Figure 5:
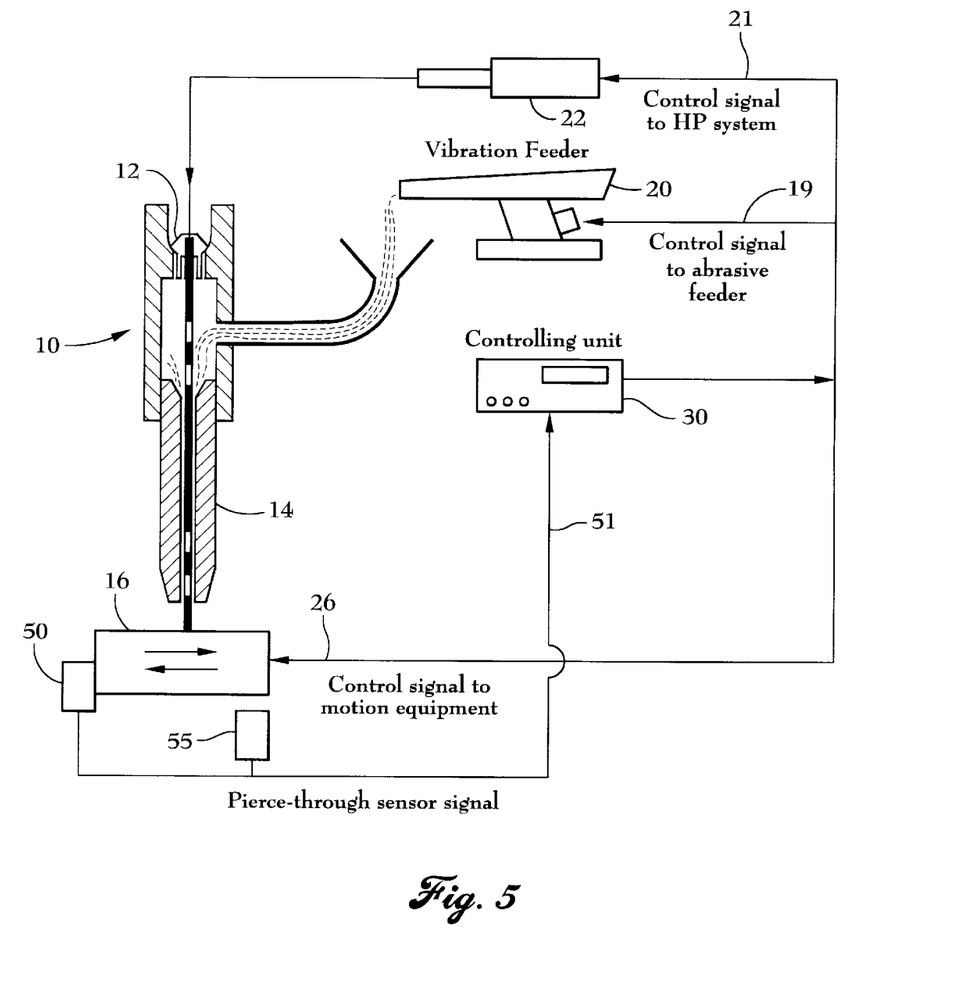
FIGS. 5 and 6 are general symbolic diagrams showing alternative embodiments of pierce-through detection devices according to the present invention.

Although described above with respect to the use of pressure sensor 42 and air supply 40 for detecting pierce time, it will be readily understood based on and upon reading the teachings of this disclosure, that other sensors may be incorporated to detect the moment of pierce-through by a waterjet. Shown in FIG. 5 are alternative pierce-through detectors 50 and 55 which, respectively, may be attached to or used in the vicinity of a workpiece 16 upon which an AWJ operation is being performed. Pierce-through detectors 50 and 55 may be used individually or in combination to provide a signal 51 to controlling unit 30 at the moment of pierce-through. Exemplary detectors which may be used in this fashion include, but are not limited to conventional sensors, which can either directly detect the presence of the waterjet upon pierce-through (e.g., by means of an optical sensor) or indirectly detect some characteristic change which occurs upon pierce through (e.g., by means of an acoustic sensor or a load cell).

Figure 3:
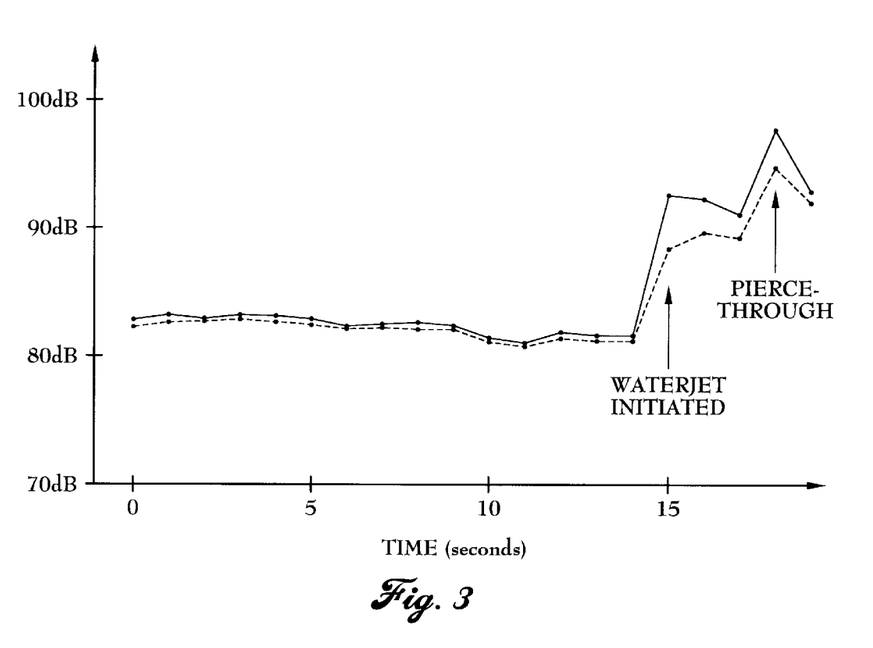
FIG. 3 shows a reproduction of the wave form actually generated by an acoustic sensor used in one embodiment of the present invention.

Acoustic sensors useful in this regard are those which can detect the change in sound level which occurs upon pierce through and include an acoustic sensor such as the Model 2800 Integrating Sound Level Meter available from Quest Technologies, Inc., Oconomowoc, Wis. Shown in FIG. 3 is a reproduction of the acoustic readings obtained during an AWJ piercing operation using an acoustic sensor with the initiation of the waterjet operation and the moment of pierce-through clearly indicated by two separate and distinct peaks. Load cells also useful in this regard are those which can detect the decrease in the force exerted on workpiece 16 by a waterjet which occurs upon pierce-through and may include load cells such as those available from Sens-All, Inc., Southington, Conn.

Figure 6:
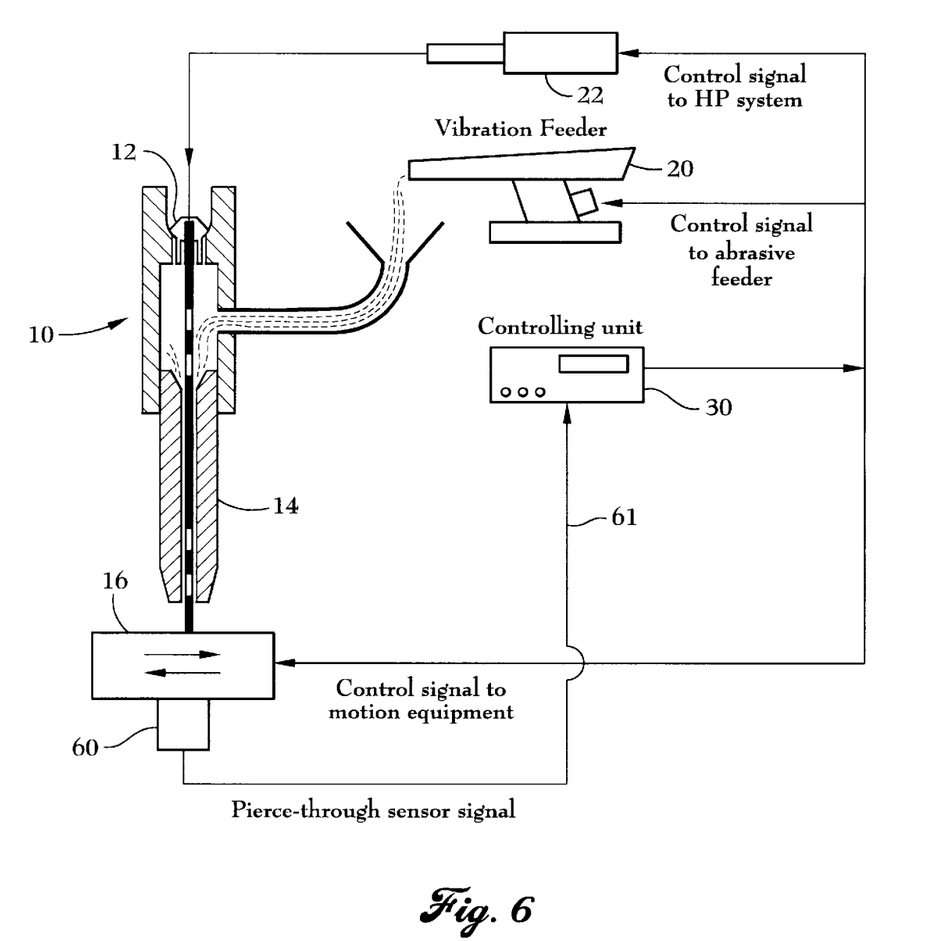

Alternatively, as shown in FIG. 6 a conventional mechanical switch 60, as is known in the art, may be located directly under workpiece 16 such that upon penetration by the waterjet, the switch 60 is tripped thereby indicating to controlling unit 30 by signal 61 the existence of a pierce-through condition.

As a result of the apparatus and method of the present invention, an AWJ system is provided which provides a number of advantages over prior art cutting and other machining processes. Among these advantages is the ability to determine using the automated machining processes according to the present invention which determine the optimum machining parameters for an AWJ operation without the need for multiple trial-and-error testing or extensive user experience for machining new materials. Moreover, the ability to "place and cut" a workpiece by using an initial starting hole as a test hole to determine the optimum cutting parameters for an AWJ cutting operation, thereby provides for a continuous operation.

Moreover, automatic programming of the machining speeds during operation may be accomplished without the need for any user interference or interface while also increasing the accuracy of the optimum machining speeds so determined. Furthermore, various control and measurement functions may be automatically accomplished using the apparatus and method of the present invention including, proximity detection of the waterjet nozzle, measuring the thickness of a workpiece, and real time monitoring and correction of nozzle stand-off distance. Additionally, compensation for changes in process parameters (e.g., changes in water pressure, abrasive flow rate, abrasive type, nozzle diameter, etc.) may also be made automatically.

ALTERNATIVE EMBODIMENTS TO ADDITIONAL MACHINING TECHNOLOGIES

Although illustrated and described herein with reference to certain specific embodiments, namely, AWJ energy beam machining processes for cutting, the present invention is nevertheless not intended to be limited to the details shown. Rather, various modifications may be made in the details in the scope and range of equivalents of the claims without departing from the spirit of the invention. For example, although the method of determining the machinability number of a material is described above with respect to piercing the material using an AWJ waterjet moved through a circular motion, it is expected that alternate patterns of piercing motions may be employed as long as Eqn. 2 is empirically correlated with the type of piercing motion pattern selected. Such alternate piercing motion patterns may include, but are not limited to, a linear, backand-forth, star, wiggle or other pattern. Other modifications may also include the application of the apparatus and method for determining the machinability numbers using other energy beam machining technologies in addition to AWJ cutting processes. Moreover, it is envisioned that the determination of machinability numbers of engineering material according to the present invention using one energy beam process may be applied to or otherwise correlated with calculating process parameters for use in other types of energy beam machining processes.

Such energy beam technologies include those which utilize a concentrated beam energy to effect material removal to cut or otherwise make, shape, prepare, or finish (i.e., machine) a raw stock material into a finished material. By way of example, it is envisioned that the apparatus and method of the present invention may be adapted for incorporation into other types of energy beam technologies, including but not limited to, pure waterjet, laser, plasma arc, flame cutting, and electron beam technologies. Although each of these use different physical phenomena to remove material, they behave similarly in nature and methodology to a waterjet energy beam such that the apparatus and method of the present invention may be employed.

Furthermore, it is to be understood that the selection of other energy beam technologies to which the present invention may be applied is not limited to these specific examples which are merely illustrative. Rather, these energy beam technologies will be readily recognized and may be selected by those having ordinary skill in the art upon analyzing the following features and as taught by the present inventor and set forth below relative to an AWJ process:

Energy Delivery Relationships:
AWJ:
The higher the applied flow/pressure (hp/watts), the faster the material removal rate.
Laser:
The higher the applied output power (hp/watts), the faster the material removal rate.
Plasma:
The higher the applied flow/pressure (hp/watts), the faster the material removal rate.

Material Removal Rate Relationships:
AWJ:
The thicker the material, the slower the cutting speed.
Laser:
The thicker the material, the slower the cutting speed.
Plasma:
The thicker the material, the slower the cutting speed.

Surface Finish Relationships:
AWJ:
The faster the cutting speed, the rougher the cut surface finish.
Laser:
The faster the cutting speed, the rougher the cut surface finish.
Plasma:
The faster the cutting speed, the rougher the cut surface finish.

Analytical Relationships:
AWJ:
Cutting and machining (e.g., turning) removal rates can be related to a machinability number.
Laser:
Cutting and machining removal rates can be related to a machinability number.
Plasma:
Cutting rates can be related to a machinability number.

Thus, it is envisioned that the method and apparatus of the present invention may be used to determine the machinability number for other energy beam processes (e.g., laser and plasma energy beam processes) which cause material responses similar to those set forth above for a waterjet process. Additionally, it is further envisioned that the energy beam processes including AWJ may be used to perform a variety of other AWJ and traditional operations such as piercing, drilling, and turning operations.

What is claimed is:

1. A method for measuring the machinability of a material, comprising the steps of:
   a) providing a material;
   b) piercing said material;
   c) simultaneously measuring a pierce time duration, T, of said piercing step; and
   d) calculating a machinability number from said pierce time duration.

2. A method for measuring the machinability of a material according to claim 1, wherein said piercing step is performed by an abrasive waterjet process.

3. A method for measuring the machinability of a material according to claim 2, wherein said step of calculating a machinability number is according to the following equation for obtaining the machinability number, $N_{mc}$, for a cutting process:

$$N_{mc} = \left( \frac{C_{tc} \cdot h^{1.786}}{T \cdot P^{1.757} \cdot d_O^{2.072}} \right).$$

4. A method for measuring the machinability of a material according to claim 3, wherein said cutting process is an abrasive waterjet cutting process.

5. A method for measuring the machinability of a material according to claim 1, wherein said piercing step is performed using a concentrated beam energy.

6. A method for measuring the machinability of a material according to claim 5, wherein said concentrated beam energy is a beam energy selected from the group consisting of an abrasive waterjet, a pure waterjet, a laser, a plasma arc, a flame, and an electron beam.

7. A method for determining the machining speed of a material, comprising the steps of:
   a) providing a material;
   b) piercing said material;
   c) simultaneously measuring a pierce time duration, T, of said piercing step;
   d) calculating a machinability number from said pierce time duration; and
   e) calculating a speed at which said material is to be machined from said machinability number.

8. A method for determining the machining speed of a material according to claim 7, wherein said piercing step is performed by an abrasive waterjet process.

9. A method for determining the machining speed of a material according to claim 8, wherein said step of calculating a machinability number is according to the following equation to obtain the machinability number, $N_{mc}$, for a cutting process:

$$N_{mc} = \left( \frac{C_{tc} \cdot h^{1.786}}{T \cdot P^{1.757} \cdot d_O^{2.072}} \right).$$

10. A method for determining the machining speed of a material according to claim 9, wherein said step of calculating a speed at which said material is to be machined is according to the following equation to obtain a cutting speed, $u_c$, for an abrasive waterjet cutting process:

$$u_c = \left( \frac{N_{mc} \cdot P^{1.593} \cdot d_O^{1.374} \cdot A^{0.343}}{C \cdot q \cdot h \cdot d_f^{0.618}} \right)^{1.15}.$$

11. A method for determining the machining speed of a material according to claim 7, wherein said piercing step is performed using a concentrated beam energy.

12. A method for determining the machining speed of a material according to claim 11, wherein said concentrated beam energy is a beam energy selected from the group consisting of an abrasive waterjet, a pure waterjet, a laser, a plasma arc, a flame, and an electron beam.

13. A method for machining a material, comprising the steps of:
   a) providing a sample comprising a material to be machined;
   b) piercing a hole through said sample;
   c) simultaneously measuring a pierce time duration, T, of said piercing step;

d) calculating a machinability number for said material from said pierce time duration;

e) calculating a speed at which a workpiece comprising said material is to be machined from said machinability number; and f) machining a workpiece comprising said material at said calculated speed.

14. A method for machining a material according to claim 13 wherein said piercing step is performed by an abrasive waterjet process.

15. A method for machining a material according to claim 14 wherein said step of machining comprises a cutting process; and said step of calculating a machinability number is according to the following equation to obtain the machinability number, $N_{mc}$, for said cutting process:

$$N_{mc} = \left( \frac{C_{tc} \cdot h^{1.786}}{T \cdot P^{1.757} \cdot d_O^{2.072}} \right).$$

16. A method for machining a material according to claim 15 wherein said step of machining comprises an abrasive waterjet cutting process; and said step of calculating a speed at which said material is to be machined is according to the following equation to obtain a cutting speed, $u_c$, for said abrasive waterjet cutting process:

$$u_c = \left( \frac{N_{mc} \cdot P^{1.593} \cdot d_O^{1.374} \cdot A^{0.343}}{C \cdot q \cdot h \cdot d_f^{0.618}} \right)^{1.15}.$$

17. A method for machining a material according to claim 16, wherein said workpiece which is machined in said machining step comprises said sample which is pierced in said piercing step.

18. A method for machining a material according to claim 13, wherein said workpiece which is machined in said machining step comprises said sample which is pierced in said piercing step.

19. A method of machining a material according to claim 13 wherein said piercing step is performed using a concentrated beam energy.

20. A method of machining a material according to claim 19 wherein said concentrated beam energy is a beam energy selected from the group consisting of an abrasive waterjet, a pure waterjet, a laser, a plasma arc, a flame, and an electron beam.

21. A method of machining a material according to claim 13 wherein said step of machining is performed using a concentrated beam energy.

22. A method of machining a material according to claim 21 wherein said concentrated beam energy is a beam energy selected from the group consisting of an abrasive waterjet, a pure waterjet, a laser, a plasma arc, a flame, and an electron beam.

23. A method of machining a material according to claim 13, wherein said step of machining is a machining operation selected from the group consisting of a piercing, a drilling, and a turning operation, and combinations thereof.

24. An apparatus for detecting the pierce time duration of a piercing force through a material which is being pierced, comprising:

a means for detecting a pierce-through condition through a material made by a piercing force;

a timing means for detecting a pierce time duration of said piercing force to create said pierce-through condition.

25. An apparatus for detecting the pierce time duration according to claim 24, wherein said means for detecting comprises:

a shield means for surrounding a source of said piercing force;

a means for supplying a gas to create a pressure within said shield means; and a sensing means for detecting a decrease in pressure caused within said shield means by said pierce-through condition created by said piercing force.

26. An apparatus for detecting the pierce time duration according to claim 25, wherein said sensing means is disposed between and in fluid communication with said means for supplying gas and said shield means.

27. An apparatus for detecting the pierce time duration according to claim 24, wherein said means for detecting a pierce-through condition is selected from the group consisting of an acoustic sensor, an optical sensor, a load cell, a mechanical switch, and combinations thereof.

* * * * *